(12) United States Patent
Hulsken et al.

(10) Patent No.: US 9,128,016 B2
(45) Date of Patent: Sep. 8, 2015

(54) UP-CONCENTRATION OF ORGANIC MICROOBJECTS FOR MICROSCOPIC IMAGING

(75) Inventors: Bas Hulsken, Eindhoven (NL); Stein Kuiper, Eindhoven (NL); Sjoerd Stallinga, Eindhoven (NL); Bo Joakim Isaksson, Eindhoven (NL); Mark W. G. Ponjee, Eindhoven (NL); Bart E. G. J. Van Meerbergen, Eindhoven (NL); Zeynep S. Unay, Istanbul (TR)

(73) Assignee: Koninklijke Philips N.V., Eindhoven (NL)

( * ) Notice: Subject to any disclaimer, the term of this patent is extended or adjusted under 35 U.S.C. 154(b) by 314 days.

(21) Appl. No.: 13/263,997

(22) PCT Filed: Apr. 14, 2010

(86) PCT No.: PCT/IB2010/051617
§ 371 (c)(1),
(2), (4) Date: Oct. 12, 2011

(87) PCT Pub. No.: WO2010/119408
PCT Pub. Date: Oct. 21, 2010

(65) Prior Publication Data
US 2012/0034623 A1    Feb. 9, 2012

(30) Foreign Application Priority Data

Apr. 14, 2009   (EP) .................................... 09305317

(51) Int. Cl.
*G01N 15/06*    (2006.01)
*G01N 1/40*    (2006.01)

(52) U.S. Cl.
CPC ............ *G01N 1/4077* (2013.01); *G01N 1/4005* (2013.01); *G01N 15/0625* (2013.01); *G01N 15/0631* (2013.01)

(58) Field of Classification Search
CPC .......... G01N 15/0625; G01N 15/0631; G01N 1/4077; G01N 1/4005
See application file for complete search history.

(56) References Cited

U.S. PATENT DOCUMENTS

| 4,948,561 | A | 8/1990 | Sullivan |
| 5,139,031 | A | 8/1992 | Guirguis |

(Continued)

FOREIGN PATENT DOCUMENTS

| DE | 3223589 A1 | 6/1982 |
| EP | 0713087 A1 | 5/1996 |

(Continued)

OTHER PUBLICATIONS

By Weigum et al.: "Cell-Based Sensor" Lab Chip, vol. 7, No. 8, Aug. 2007, pp. 995-1003, XP002550801.

(Continued)

*Primary Examiner* — Melanie Y Brown

(57) ABSTRACT

A method of analyzing a sample fluid containing organic microobjects is proposed. The method comprises the steps of: up-concentrating (S1) the microobjects by removing, in a total time $T_1$, a volume $V_1$ of the sample fluid from the upconcentrate sample microobjects; immersing (S2) the microobjects in a transfer fluid, or leaving the microobjects in a remaining portion of the sample fluid, the remaining portion of the sample fluid then providing the transfer fluid; filtering (S3), in a total time $T_3$, a volume $V_3$ of the transfer fluid by a filter, thereby accumulating the microobjects on the filter; and generating (S4) an image of the microobjects accumulated on the filter; wherein the throughput $V_1/T_1$ of the step of up-concentrating (S1) is greater than the throughput $V_1/T_1$ of the step of filtering (S3). The filter may be a second filter, and the step of up-concentrating (S1) may involve: filtering the sample fluid by a first filter, thereby accumulating the microobjects on the first filter. An apparatus or system for analyzing a sample fluid containing organic microobjects is also disclosed.

13 Claims, 14 Drawing Sheets

(56) References Cited

U.S. PATENT DOCUMENTS

| | | | |
|---|---|---|---|
| 5,897,993 | A | 4/1999 | Sato et al. |
| 6,418,799 | B1* | 7/2002 | Pardue et al. ............. 73/863.21 |
| 6,562,583 | B1 | 5/2003 | Herbig |
| 2002/0164670 | A1 | 11/2002 | Forrest |
| 2003/0178507 | A1* | 9/2003 | Maria Rijn Van ............. 239/337 |
| 2003/0186428 | A1 | 10/2003 | Guillot |
| 2005/0221403 | A1 | 10/2005 | Gazenko |
| 2005/0277203 | A1 | 12/2005 | Niskanen |
| 2007/0025883 | A1 | 2/2007 | Tai |
| 2007/0196884 | A1* | 8/2007 | Bodini et al. ................... 435/18 |
| 2008/0190219 | A1* | 8/2008 | Jensen et al. ............... 73/864.71 |
| 2010/0255560 | A1* | 10/2010 | Call et al. ...................... 435/243 |
| 2012/0202210 | A1* | 8/2012 | Burroughs et al. .......... 435/6.12 |
| 2012/0264155 | A1* | 10/2012 | Frandsen et al. ................ 435/23 |

FOREIGN PATENT DOCUMENTS

| | | |
|---|---|---|
| EP | 0713987 B1 | 5/2001 |
| FR | 2809969 A1 | 6/2000 |
| JP | 62121332 A | 6/1987 |
| JP | 63053447 | 3/1988 |
| JP | 02006729 | 1/1990 |
| JP | 02006729 A | 1/1990 |
| JP | 2005152849 A | 6/2005 |
| JP | 2007111653 A | 5/2007 |
| WO | 9822618 A1 | 5/1998 |

OTHER PUBLICATIONS

By Fluxxion: "Fluxxbox" Internet Article, [Online] Aug. 2004, pp. 1-2, XP002550802 Retrieved from the Internet: URL : http ://www. fluxxion.com/LF_fluXXbox.pd [retrieved on Oct. 13, 2009] Fluxxbox system documentation, Dated Aug. 2004.

* cited by examiner

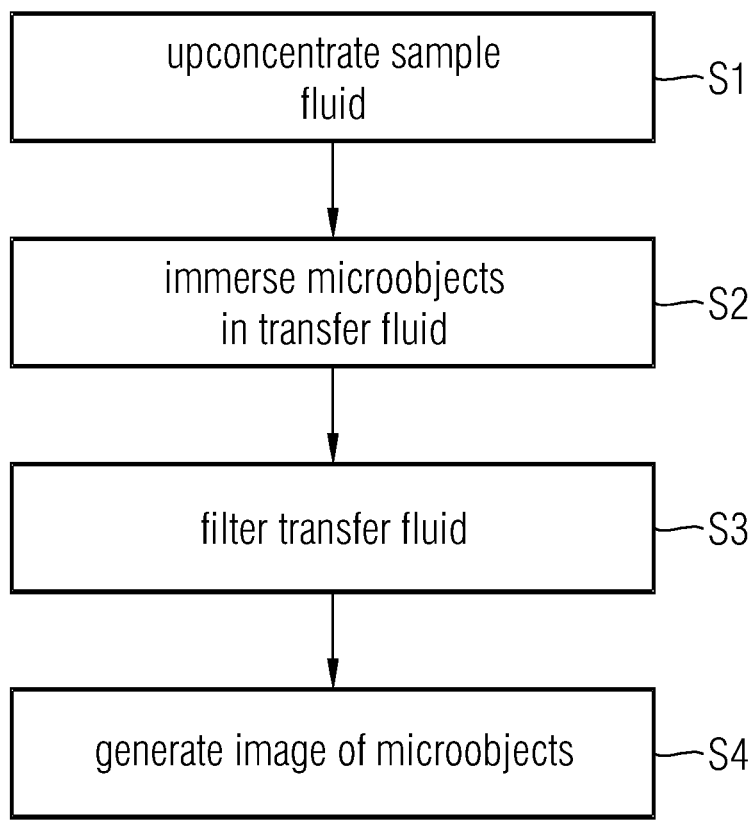

UP-CONCENTRATION OF ORGANIC MICROOBJECTS FOR MICROSCOPIC IMAGING

FIELD OF THE INVENTION

In a first aspect, the invention relates to a method of analyzing a sample fluid containing organic microobjects.

In a second aspect, the invention relates to an apparatus or system for analyzing a sample fluid containing organic microobjects.

BACKGROUND OF THE INVENTION

The invention relates to the field of microbiology, in particular to microbiological analysis of fluid samples. In general, such analysis is aimed at determining the presence/absence of specific organic microobjects in the sample, at quantifying their number or concentration, and in some cases at identifying an unknown microorganism to various levels of detail. The term "organic microobject" may refer to any object of a large variety of microscopic objects of biological origin, in particular microorganisms and cells. Microorganisms include bacteria, fungi, archaea, protists, green algae, animals such as plankton, the planarian and the amoeba. Cells include, apart from bacteria, plant cells and mammalian cells, e.g. blood cells and tissue cells. Besides clinical diagnostics, such as testing of sputum or other bodily fluids, microbiological analysis has important industrial applications, for example in the food and beverage, pharmaceutical, personal care products, and environmental sectors. Current standard methods of testing are based on cell culturing and have time to results of days to weeks depending on the type of sample and microorganism. There is a need for microbiological analysis with increased throughput.

An example of such a rapid method is the one proposed by AES Chemunex (www.aeschemunex.com). Their FDA-approved ScanRDI-system provides a throughput from sample to result of 90 minutes and performs the analysis by laser scanning cytometry of filtered products. The steps of this method are: filtering the fluid sample, staining the possibly present microbiological contaminants with a fluorescent dye, optically scanning the surface of the filter with a large laser spot (5-10 μm) for detecting the possibly present microbiological contaminants, and imaging the areas surrounding the contaminants with a high-resolution (0.5 μm) microscope with an automated stage. The technique has been described in J. -L. Drocourt, P. Desfetes, J. Sanghera, Apparatus and process for rapid and ultrasensitive detection and counting of microorganisms by fluorescence, EP 0713087 B1 (1994).

An improved filter technology is provided by fluXXion (www.fluxxion.com). The technology is based on lithographically defined microsieves, which have a single well-defined pore size (down to 0.2 μm), are optically flat (which is advantageous from the point of view of the subsequent optical scanning step and also results in reduced backscattering) and thin so as to offer a low flow resistance and hence a higher filtration throughput compared to conventional membrane filters made from porous materials such as cellulose, nylon, polyvinyl chloride, polysulfone, polycarbonate, and polyester. An alternative to the two steps of low resolution imaging (via laser spot scanning) and high resolution imaging (with a microscope) is imaging the whole filter area at high resolution. In order to have a reasonable throughput for filtering it turns out that the filter area is much larger than the field of view of standard microscope objectives with the required resolution. For example, a resolution of 0.5 μm typically requires a 40X/NA0.65 objective lens with a field of view with a diameter of 0.5 mm. Typical filters have a diameter of several mm, so about an order of magnitude larger than the microscope objective lens. Clearly, this requires scanning the filter area, which is time-consuming and needs complex mechanics with high accuracy.

In a related context, rapid detection of pathogens and testing for antibiotic resistance/susceptibility can be crucial for proper treatment of patients with an infectious disease. Classical culturing techniques with patient samples typically take several days from sampling to end-result and have to be performed in large central microbiology labs. During this time, the patient can usually not remain untreated without suffering from severe consequences, which limits the medical practitioners to a guessing game using a broad antibiotic spectrum. This is not only economically costly but also increases the problems of antibiotic-resistive bacterial strains in hospital environments.

Speed can be gained and costs may be reduced by using automated and integrated tests on microfluidic devices. Speed may further be gained and costs may further be reduced by reducing the size of micro fluidic devices, to implement small reagent volumes and enable use of single-use plastic cartridges. A microfluidic system generally comprises a fluidic system into which the sample can be injected. It may further contain means for enriching bacteria and for separating them from human cells. The human cells may be examined separately in ways that would otherwise interfere with the bacterial analysis. Some microfluidic devices are adapted for screening mammalian cells for the presence of viral genes. Such devices may be capable of detecting all known types of microscopic pathogens. Microfluidic techniques have a great potential for rapid diagnosis of infectious diseases, for example by looking at a gene profile with e.g. real-time PCR, or through culturing in the microfluidic device and analysis of single bacterial divisions. There are various micro fluidic techniques for separating bacteria from human cells.

Examples include electrophoresis (see A. K. Balasubramanian, K. A. Soni, et al., A microfluidic device for continuous capture and concentration of microorganisms from potable water, Lab on a Chip, vol. 7, pp. 1315-1321, 2007), dielectrophoresis (see L. J. Yang, P. P. Banada, et al., A multifunctional micro-fluidic system for dielectrophoretic concentration coupled with immuno-capture of low numbers of listeria monocytogenes, Lab on a Chip, vol. 6, pp. 896-905, 2006) and magnetic bead separation (see Y. K. Cho, J. G. Lee, et al., One-step pathogen specific DNA extraction from whole blood on a centrifugal microfluidic device, Lab on a Chip, vol. 7, pp. 565-573, 2007).

However, a microfluidic device generally has a very limited sample throughput, typically on the order of a few μl/min. For that reason, there is a severe mismatch with real patient samples, such as from an oral or nasal swab, which often contain only 100 or less of the relevant bacteria in e.g. 1 ml of liquid, or blood samples containing several ml of liquid (typically 5-10 ml) and only a few free floating bacteria. Typically, real patient samples contain only a total of 10 to 100 of the relevant bacteria in 1 to 5 ml of sample liquid. Using only a fraction of the sample is therefore not an option. However, a ml volume does usually not fit into a microfluidic device. A connection between a macrofluidic sample volume and a microfluidic system is therefore required.

In addition to the above mentioned microfluidic techniques for separating bacteria and human cells in μl volumes, there are also many ways of doing this on the laboratory bench. A simple approach is to use syringe filters or centrifuge filters from e.g. Sartorius Stedim (www.sartorius-stedim.com), Whatman (www.whatman.com) or Millipore (www.millipore.com). Large pore-sizes capture the human cells while smaller pores catch the pathogens.

Wiegum and co-workers (S. E. Weigum, P. N. Floriano, et al., Cell-based sensor for analysis of EGFR biomarker expression in oral cancer, Lab. on a Chip, vol. 7, pp. 995-1003, 2007) have integrated filters in a PMMA cartridge and filtered out cells, which are then analyzed on a membrane. Here, the flow speeds are quite high, 250 µl/min-750 µl/min, but the cells, which are captured on the filter membrane, are not transferred to another liquid volume for further analysis.

Wu and Kado have used filters to enrich bacterial DNA in a sample (S. J. Wu and C. I. Kado, Preparation of milk samples for PCR analysis using a rapid filtration technique, Journal of Applied Microbiology, vol. 96, pp. 1342-1346, 2004). The authors use a filter with a 0.4 µl tm pore size to capture bacteria from a sample of milk. The membrane with the bacteria is then treated with a lysis buffer and the DNA is subsequently used for PCR. The very simple technique has a sensitivity of about 10 colony forming units (CFU) per ml of milk. For DNA analysis, there are also special centrifugation filters from SIRS-Lab (www.sirs-lab.com) which separate bacterial and human DNA. However, although efficient on the bench, none of the techniques above have been directly connected to a microfluidic chip.

Other methods of analysis include fluorescence activated cell sorting (FACS) or magnetic activated cell sorting (MACS), where the bacteria are labeled with antibodies for a specific strain and then sorted out. FACS machines can have a reasonably high throughput but are large and complex instruments and require specific labeling with antibodies. Magnetic separation of either the labeled cells or DNA bound to e.g. silica magnetic beads can be used to transfer the pathogen or pathogen DNA to a much smaller volume in a funnel structure. Nevertheless, the incubation of beads and sample still has to occur in a large volume, which is time consuming. Also, the transfer of the magnetic beads themselves, bound to cells or DNA, may also be problematic within the microfluidic system.

It is an object of the invention to reduce the total time that is required for imaging organic microobjects that are initially contained in a sample fluid.

SUMMARY OF THE INVENTION

According to the first aspect of the invention, the method of analyzing a sample fluid comprises the steps of:
  up-concentrating the microobjects by removing, in a total time $T_1$, a volume $V_1$ of the sample fluid from the microobjects;
  immersing the microobjects in a transfer fluid; or leaving the microobjects in a remaining portion of the sample fluid, the remaining portion of the sample fluid then providing the transfer fluid;
  filtering, in a total time $T_3$, a volume $V_3$ of the transfer fluid by a filter, thereby accumulating the microobjects on the filter; and
  generating an image of the microobjects accumulated on the filter;
wherein the throughput $V_1/T_1$ of the step of up-concentrating is greater than the throughput $V_3/T_3$ of the step of filtering. Thus the step of up-concentrating is fast compared to the step of filtering. The invention thus proposes a two-step approach, in which a portion of the sample fluid is removed from the microobjects using a fast technique before the microobjects are collected on the filter. Of course, the two-step approach could be extended to involve additional steps. The volume $V_1$ may be the total volume of the sample fluid or a fraction thereof Similarly, the volume $V_3$ may be the total volume of the transfer fluid or a fraction thereof. The throughput $V_1/T_1$ and the throughput $V_3/T_3$ are average throughputs, as they may be computed from the instantaneous throughputs (i.e. from the instantaneous volumetric rates of change) associated with the sample fluid and with the transfer fluid, respectively, by averaging the instantaneous rates of change over the times $T_1$ and $T_3$, respectively. The respective instantaneous throughputs may, but do not necessarily have to be, substantially constant during the steps of up-concentrating and of filtering, respectively. The throughput $V_1/T_1$ may, for example, be more than 3, 10, 30, 100, 300, 1000, or 3000 times greater than the throughput $V_3/T_3$ The time $T_2$ spent on the step of immersing may be negligible compared to the step of up-concentrating. For example, the time $T_2$ spent on the step of immersing may be less than 10%, 3%, or 1%, of the time $T_3$ spent on the step of up-concentrating. Thus, compared to a conventional method, in which substantially all the sample fluid is removed from the microobjects by filtering the entire sample fluid through the filter, the total time of the procedure can be reduced. Stated equivalently, the filter may have a lower throughput as compared to the filter used in the conventional method, the lower throughput being compensated for by the smaller quantity of sample fluid that needs to flow through the filter. Given the same amount of time, the filter can thus be smaller, for example, so as to fit into the field of view of an optical microscope, avoiding a need for scanning the filter and thus further reducing the total amount of time. The transfer fluid may have a volume of less than 20%, less than 10%, less than 5%, or less than 1% of the initial volume of the sample fluid. In the step of removing, more than 70%, more than 90%, more than 95%, or more than 99% of the sample fluid may be removed from the microobjects. Thus the concentration of the microobjects is considerably increased before the step of filtering.

The time $T_1+T_2+T_3+T_4$ spent on the steps of up-concentrating, immersing, filtering, and generating the image may be shorter than the time spent on filtering the entire sample fluid by the filter and imaging the microobjects on that filter. Herein it is understood that the same imaging method is used.

The volume $V_3$ of the transfer liquid that is filtered by the filter may be significantly smaller than the volume $V_1$ that is removed from the microobjects. For example, $V_3$ may be less less than one of the following: $0.3*V_1$, $0.1*V_1$, $0.03*V_1$, $0.01*V_1$, $0.003*V_1$, and $0.001*V_1$. Thus the total time $T_1+T_2+T_3+T_4$ of the method may be considerably reduced. In fact, the larger the fraction of the sample fluid that is removed in the fast up-concentration step, the shorter the total time of the procedure may be expected to be.

The method may comprise a step of
  prefiltering the sample fluid by a prefilter, the prefilter retaining at most an insignificant fraction of the microobjects;
the step of prefiltering being performed prior to the step of filtering. Thus, objects (e.g. mammalian cells) larger than the microobjects of interest (e.g. bacteria) may be filtered out beforehand, facilitating the subsequent analysis.

The filter may be a second filter and the step of up-concentrating may involve
  filtering the sample fluid by a first filter, thereby accumulating the microobjects on the first filter.
According to this embodiment, the step of up-concentrating is also performed by filtering. While the second filter may be particularly adapted for filtering a small volume, the first filter may be particularly adapted for filtering a large volume. For example, the first filter may be larger than the second filter.

The method may further comprise:
dissolving the first filter.

Once the first filter has been dissolved, the microobjects may be transferred more easily to the second filter. The first filter may be dissolved by, e.g., the transfer fluid.

The step of immersing may involve:
the transfer fluid flowing along the first filter; or
a portion of the sample fluid flowing back through the first filter.

In the latter case, i.e. in the case of a portion of the sample fluid flowing back through the first filter, the transfer fluid is provided by the sample fluid. In both cases the transfer fluid will carry the microobjects with it. The transfer fluid may then be channeled to the second filter.

The step of up-concentrating may involve:
evaporating the volume $V_1$ of the sample fluid; and/or
attracting the microobjects to a collection zone; and/or
centrifugalizing the sample fluid.

Thus, alternative ways of concentrating the microobjects are provided.

Generating the image may involve
generating an optical image of the microobjects; or
scanning the microobjects.

This can be done by any method known in the art, using e.g. the method by AES Chemunex described above.

The method may further comprise
releasing a dye to the sample fluid or to the transfer fluid.

Thus the microobjects can be stained before, during or after the up-concentration process. The dye may be embedded in the first filter, in particular if the first filter is to be dissolved. Alternatively, the dye may be contained in a coating of the first filter. Alternatively, it could be contained in the prefilter (if present) or in the second filter, or it could be released otherwise. The method may further comprise:

releasing a deactivating agent for deactivating dye, to the sample fluid or to the transfer fluid. The deactivating agent may be embedded in the first filter or in the second filter, or could be released otherwise.

The apparatus or system according to the second aspect of the invention comprises:

means for up-concentrating the microobjects by removing, in a total time $T_1$, a volume $V_1$ of the sample fluid from the microobjects;

means for immersing the microobjects in a transfer fluid, or for leaving the microobjects in a remaining portion of the sample fluid, the remaining portion of the sample fluid then providing the transfer fluid;

means for filtering, in a total time $T_3$, a volume $V_3$ of the transfer fluid by a filter, to accumulate the microobjects on the filter; and means for generating an image of the microobjects accumulated on the filter;

wherein the throughput $V_1/T_1$ of the means for up-concentrating is greater than the throughput $V_3/T_3$ of the filter. Thus, a total assay time may be reduced. The system or apparatus may comprise an optical microscope for generating an optical image of the microobjects accumulated on the filter.

The filter may be a second filter and the means for up-concentrating may comprise a first filter for retaining the microobjects, the first filter having a larger area than the second filter. In this context, the term "area" has the usual meaning given to it in the art, i.e. it refers to that part of the surface of the filter that is to be exposed to the fluid entering the filter. Parts of the surface of the filter which are not intended to be exposed to the inflowing fluid do not contribute to the area of the filter. For example, the area of the first filter may be more than 3, 10, 30, 100, 300, 1000, 3000, or 10000 times larger than the area of the second filter. Thus the first filter may have a considerably greater maximum possible throughput than the second filter. The first filter and the second filter may have the same pore size and/or the same pore structure, e.g. the same pore geometry. For example, the first filter and the second filter may be made of the same kind of material. The first filter and the second filter may be membrane filters differing substantially only in their area, the first filter having a larger area than the second filter. The first filter and the second filter may be circular membrane filters differing only in their diameter, the first filter having a larger diameter than the second filter.

The filter may be a second filter and the means for up-concentrating may comprise a first filter for retaining the microobjects, the first filter having a higher maximum throughput than the second filter. For example, the first filter may have a larger effective filtering area than the second filter. Alternatively or additionally, the means for up-concentrating may, for example, comprise a centrifuge for centrifugalizing the sample fluid, or an evaporator for evaporating at least a substantional portion of the sample fluid, or an attractor for attracting the microobjects to a collection zone.

The first filter may comprise a dye for staining the microobjects. The dye may be contained in a coating of the filter. Upon exposing the filter to a to-be-analyzed liquid, the dye would be released into the liquid. In the case of a soluble filter, the dye could be embedded in the filter. It would be released when the filter is dissolved. Furthermore, the dye may be contained in coating of the soluble filter, and the filter may contain a substance for deactivating the dye embedded in the filter.

The first filter may comprise a perforated aluminum foil or an organic polymer that is soluble in an organic solvent. Thus the first filter could be dissolved after the microobjects have accumulated on it.

The system or apparatus may comprise a micro fluidic chip comprising the filter. The microfluidic chip could have an optical window through which the microobjects could be imaged. It could further be adapted for performing other assays, e.g. chemical assays, on the microobjects.

BRIEF DESCRIPTION OF THE DRAWINGS

FIG. 5 is a flow chart of a method of analyzing a sample fluid containing organic microobjects.

DETAILED DESCRIPTION OF THE INVENTION

Figure 1A:
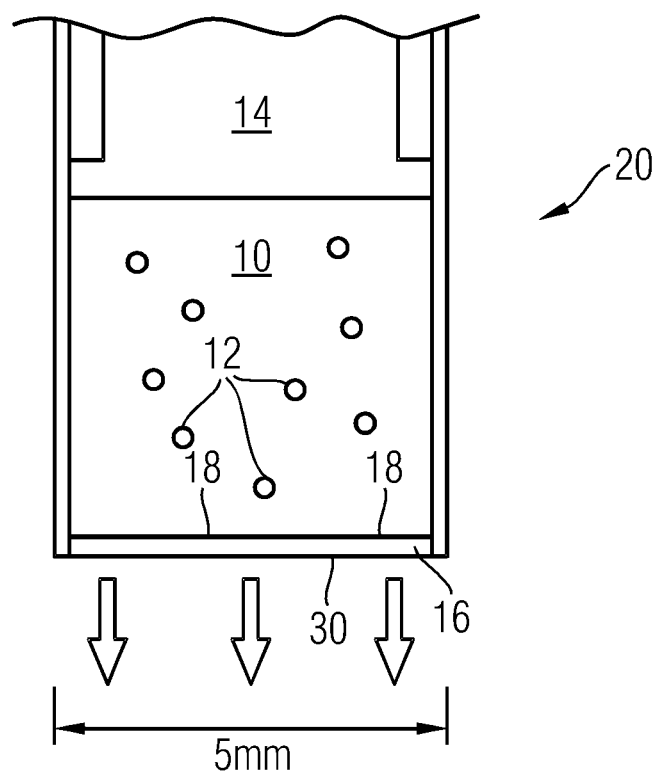
FIG. 1 schematically illustrate accumulating microobjects using a first filter and a syringe.

Unless specified otherwise, identical or similar reference numerals appearing in different Figures refer to identical or similar components.

According to a preferred embodiment of the invention, a method for rapid microbiological analysis comprises steps for preparing the sample, for up-concentration, for staining the micro-organisms with a (fluorescent) dye, for microscopic imaging, and for image analysis, in which the steps for up-concentration comprise a first step for filtering with a large area filter, and a second step for collecting the filter residue (including the possibly present micro-organisms) onto a small area, such that this small area matches the field of view a microscope objective with the required resolution for microscopic imaging, for example a 40X/NA0.65 objective with a field of view of 0.5 mm and allowing for imaging with 0.5 µm resolution. The method allows for microscopic imaging with a single capture (exposure) and so avoids scanning, while at the same time the overall throughput is high because of the first filtering step with a large area filter (filter time is inversely proportional to filter area). In other words, a large volume of sample fluid is quickly filtered thanks to the large surface area of the first filter, and thereafter the second filtration is also quick despite the small area of the second filter because the volume of the sample has been reduced in the first filtering step (up-concentration).

In a first embodiment the large area filter is made of soluble material, and in the second step a solvent is used for dissolving the filter that does not affect bacteria. More precisely, the large area filter is made of a material that is insoluble in the fluid to be examined (usually water-based), but soluble in other solvents. Preferably, the material does not affect the (stained) bacteria. An example could be perforated aluminum foil. The foil does not dissolve in water, but would dissolve in vinegar (diluted acetic acid). Vinegar does not dissolve bacteria. Other examples could be filters made of organic polymers that are affected by organic solvents, e.g. organic polymers which disintegrate when brought into contact with the organic solvent. In the first step the fluid sample is filtered over the large-area filter and in the second step the filter including bacteria is dissolved in the second fluid. The resulting liquid sample is smaller in volume than the original sample and can thus be filtered with a small area filter that is not soluble in the second fluid (e.g. a ceramic filter) in a relatively short time span.

In a second embodiment the pumping direction is reversed after the first filtering step and a small part of the fluid and all retained micro-organisms are directed towards a small area filter.

In a third embodiment a lateral flow is induced after the first filtering step such that the filter residue is collected onto a sub-area of the filter.

In all of these embodiments a dye, in particular a fluorescent dye, may be added to the fluid during the filtering, so that the micro-organisms are stained during the filtering steps. A preferred embodiment of this would be to include the dye in at least one of the filters. There are several methods for doing this:

(a) Adding the dye as a coating to the filter. Upon exposing the filter to the to-be-analyzed liquid, the dye is released into the liquid.

(b) In the case of a soluble filter (embodiment 1), the dye can be embedded in the filter. Thus it is released when the filter is dissolved.

(c) Adding the dye as a coating, as in (a), and adding a substance that deactivates the dye embedded in the soluble filter, as in (b). An advantage would be that the dye (except the dye taken up by the bacteria) becomes deactivated when the filter is dissolved, so that no bacterial contaminants which arrive after the first filtering step will be stained. This allows for a non-sterile second filtering pass.

Figure 1B:
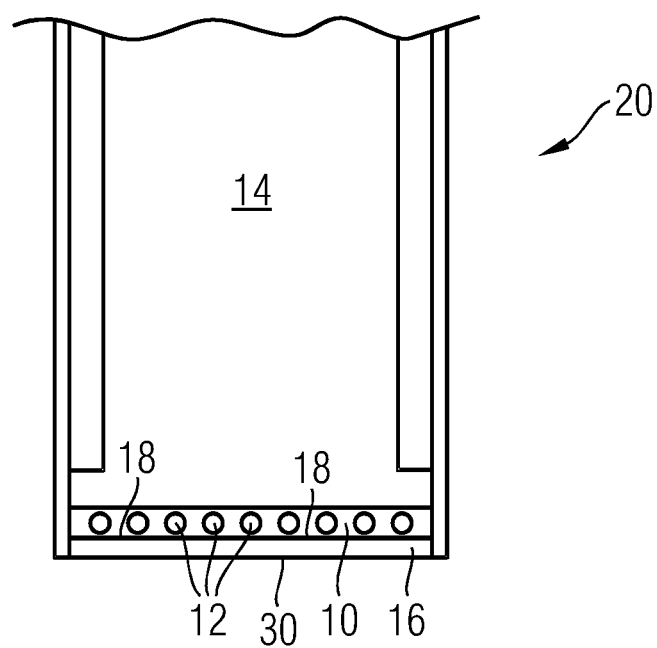

Shown in FIG. 1 is a device 20 for concentrating organic microobjects 12 contained in a sample fluid 10. The sample fluid 10, of macroscopic volume, is contained in a chamber of the device 20, as shown in FIG. 1a. By pushing a syringe piston 14 toward a first filter 16, the sample fluid 10, or at least a substantial portion of it (e.g., at least 50%, or at least 80%, or at least 90%) is forced through the filter 16. The microobjects 12 are retained by the first filter 16 and accumulate on a surface 18 of the first filter 16 (see FIG. 1b). Thereby at least 50%, or at least 80%, or at least 90%, or at least 99% of the sample fluid 10 is removed from the microobjects 12. It may be noted that the sample fluid 10 may contain smaller microobjects not shown in the Figure which may pass through the filter 16. In a subsequent step (not shown), the microobjects 12 are immersed in a transfer fluid having a smaller volume than the sample fluid 10. The transfer fluid is then filtered by a second filter 32 (represented in FIG. 4) to accumulate the microobjects 12 on a surface 34 of the second filter 32. The transfer fluid may be provided by a portion of the sample fluid 10 that has flown through the first filter 16, or by another fluid, or by a mixture of the sample fluid 10 and another fluid. After accumulating the microobjects 12 on the second filter 32 (see FIG. 4), they may be detected or imaged by any suitable method, e.g. by scanning microscopy. The first filter 16 may be designed such that the step of up-concentrating more than half of the sample fluid 10 from the microobjects takes less time than the step of filtering the transfer fluid by the second filter 32. This may be achieved, for example, by choosing the first filter 16 sufficiently large.

Figure 2A:
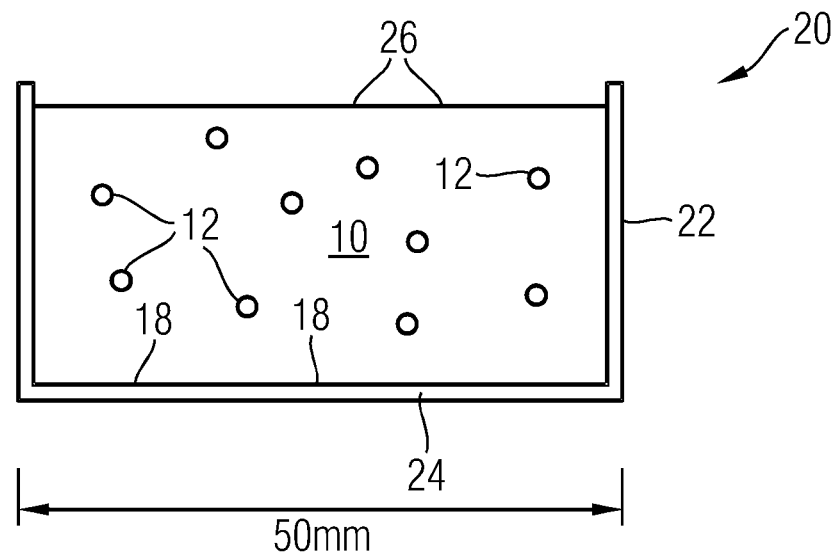
FIG. 2 schematically illustrate accumulating microobjects using evaporation.
Figure 2B:
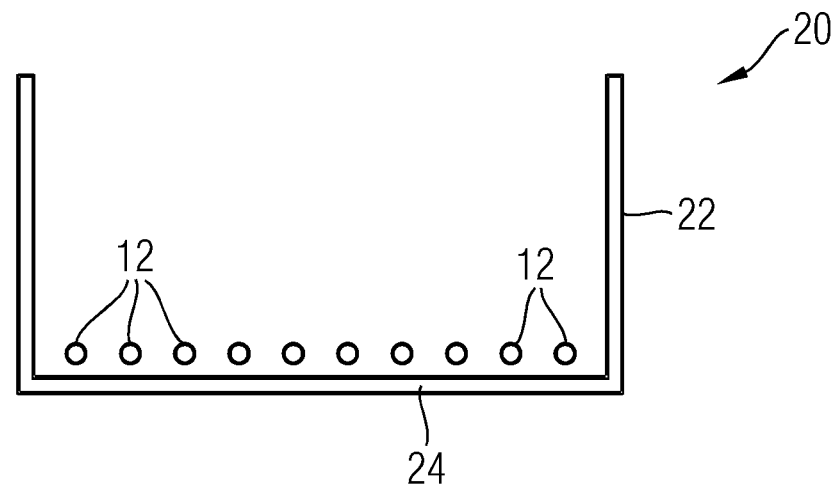

Referring now to FIG. 2, there is illustrated an alternative method of removing all or a substantial portion of the sample fluid 10 from the microobjects 12, in the case where the sample fluid 10 is a liquid. A device 20 comprises a basin having side walls 22 and a bottom plate 24. The sample liquid 10 containing the microobjects 12 is introduced into the basin 20, as shown in FIG. 2a. The sample liquid 10 has a surface 26 forming an interface between the sample liquid 10 and air or vacuum or another gas. At the surface 26 (evaporation surface) the sample liquid 10 evaporates. The sample liquid 26 may be heated in order to accelerate the evaporation process. Alternatively or additionally, the air/gas contacting the sample liquid 10 at the evaporation surface 26 may be heated, or a hot flow of air/gas along the evaporation surface 26 may be generated. As the sample liquid 26 evaporates, the microobjects 12 accumulate on the bottom plate 24 of the basin 20, as shown in FIG. 2b. In a subsequent step, already described above with reference to FIG. 1, the microobjects 12 are transferred to the second filter 32 shown in FIG. 4 and imaged. Again, the proposed method may require a smaller total amount of time as compared to filtering the entire sample liquid 10 by the second filter 32.

Figure 3A:
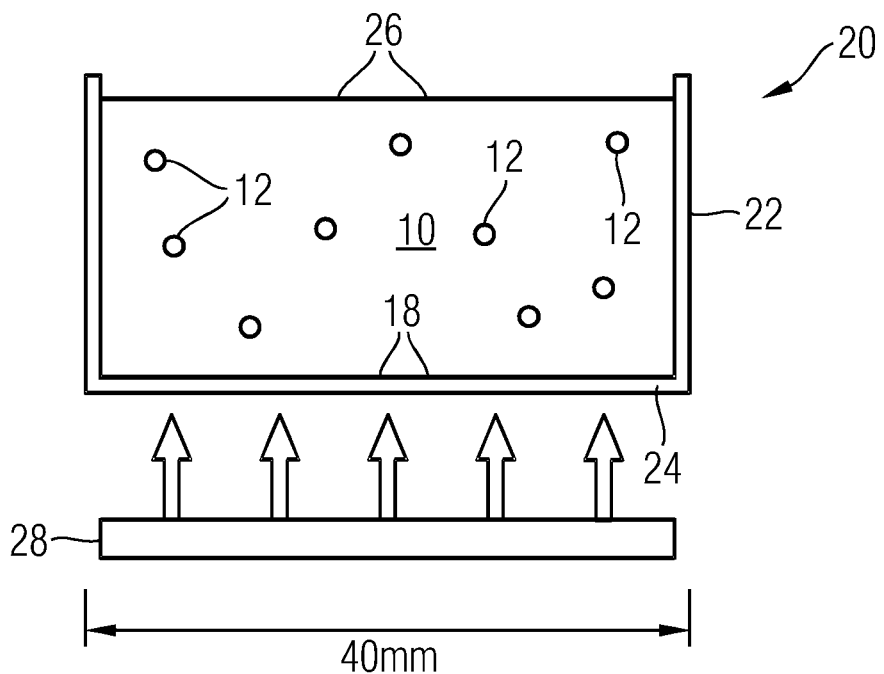
FIG. 3 schematically illustrate accumulating microobjects by attracting the microobjects toward a surface.
Figure 3B:
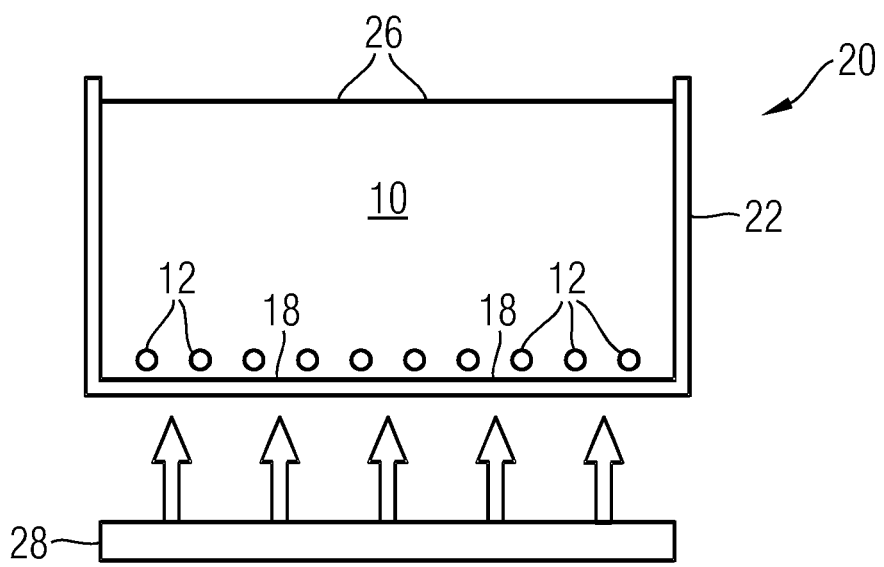
Figure 3C:
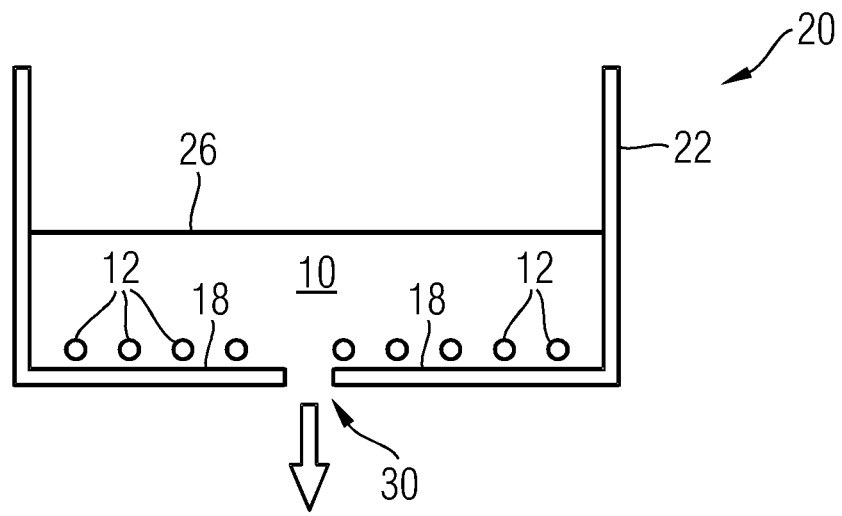

FIG. 3 illustrates another method of removing all or a substantial portion of the sample fluid 10 from the microobjects 12, in the case where the sample fluid 10 is a liquid. The sample liquid 10 is contained in a basin having a transparent bottom plate 24. A light source 28 is arranged below the bottom plate 24 to emit light via the bottom plate 24 into the basin, as illustrated in FIG. 3a. The light attracts light-sensitive microorganisms 12 toward the bottom plate 24, as shown in FIG. 3b, where they accumulate. Alternatively, instead of using a light source, an electrical field may be applied across the sample liquid 10 to attract charged microobjects, for example, negatively charged bacteria, to the bottom plate 24. In a subsequent step, shown in FIG. 3c, the sample fluid 10 is released through a macrofluidic outlet 30, the microobjects remaining behind on the bottom plate 24. In a subsequent step, already described above with reference to FIG. 1, the microobjects 12 are transferred to the second filter 32 shown in FIG. 4 and imaged. Again, the proposed method may require a smaller total amount of time as compared to filtering the entire sample liquid 10 by the second filter 32.

Figure 4:
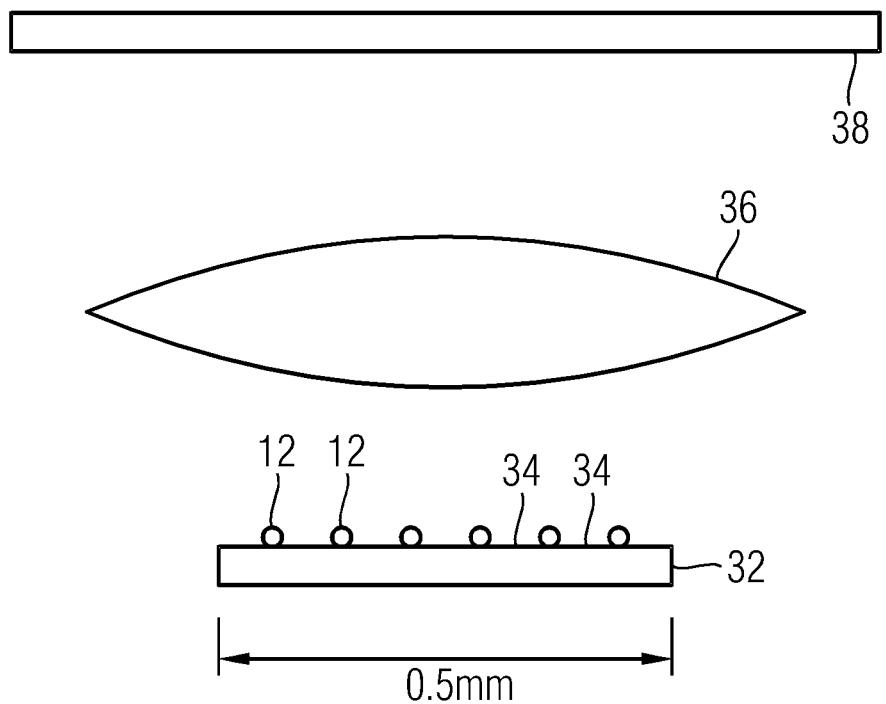
FIG. 4 schematically shows a setup for imaging microobjects on a second filter.

Shown in FIG. 4 is a simplified representation of an exemplary imaging system for imaging the microobjects 12 accumulated on the surface 34 of the second filter 32. The entire second filter 32 fits into the field of view of a microscope objective 36 shown in the Figure as a single lens, but usually comprising a lens system. The microscope objective 36 generates an optical image of the microobjects 12 on an image sensor 38. The image sensor 38 may, for example, comprise a charge coupled device (CCD). The image sensor 38 is coupled to an information processing device (not shown), for example, a personal computer, for processing an output signal delivered by the image sensor 38.

FIG. 5 represents a flow chart of a method of analyzing a sample fluid containing organic microobjects. The method comprises the successive steps of:
- up-concentrating (S1) the microobjects by removing, in a total time $T_1$, a volume $V_1$ of the sample fluid 10 from the microobjects 12;
- immersing (S2) the microobjects in a transfer fluid; or leaving the microobjects in a remaining portion of the sample fluid, the remaining portion of the sample fluid then providing the transfer fluid;
- filtering (S3), in a total time $T_3$, a volume $V_3$ of the transfer fluid by the filter 32, thereby accumulating the microobjects on the filter; and
- generating (S4) an image of the microobjects accumulated on the second filter.

In the method, the throughput $V_1/T_1$ of the up-concentration step S1 is greater than the throughput $V_3/T_3$ of the filtering step S3. The times spent on the steps of up-concentrating S1, immersing S2, filtering S3, and generating the image S4 are $T_1$, $T_2$, $T_3$, and $T_4$, respectively. Note that the total time $T_1+T_2+T_3+T_4$ spent on the steps of up-concentrating S1, immersing S2, filtering S3, and generating the image S4 can be considerably shorter than the total time $T_3'+T_4'$ that would be spent on filtering the entire sample fluid 10 by the filter 32 and imaging the microobjects 12 on that filter 32.

Referring now to FIGS. 6 to 11, these Figures illustrate different designs of a device for reducing a macroscopic (ml) sample volume to a microscopic volume (μl) that can be further transferred into a microfluidic system, while still containing the initial amount of pathogens. The concentration of pathogens is highly increased as the sample volume decreases. A prefilter may be arranged for separating out human cells before the sample enters the microfluidic chip, in order to facilitate downstream analysis processes and to obtain a maximum amount of relevant data from both a bacterial and a mammalian analysis. The prefilter may in particular increase the sensitivity of the subsequent on-chip analysis. Furthermore, it is proposed to combine macroscopic physical filters or membranes of different pore sizes with a micro fluidic system.

In particular, it is proposed to combine one or more macrofluidic filters with a microfluidic system, in order to harvest bacteria, fungi or yeast from a large volume and elute in a microfluidic volume, thereby enriching the concentration of the above mentioned pathogens and decreasing the sample volume for further processing. Preferably, the invention consists of at least two filters, where the first one has a larger pore-size to filter out e.g. human cells that are not needed for the downstream analysis while passing through the bacteria of interest and the second filter has a pore-size smaller than the size of the bacteria of interest.

Figure 6A:
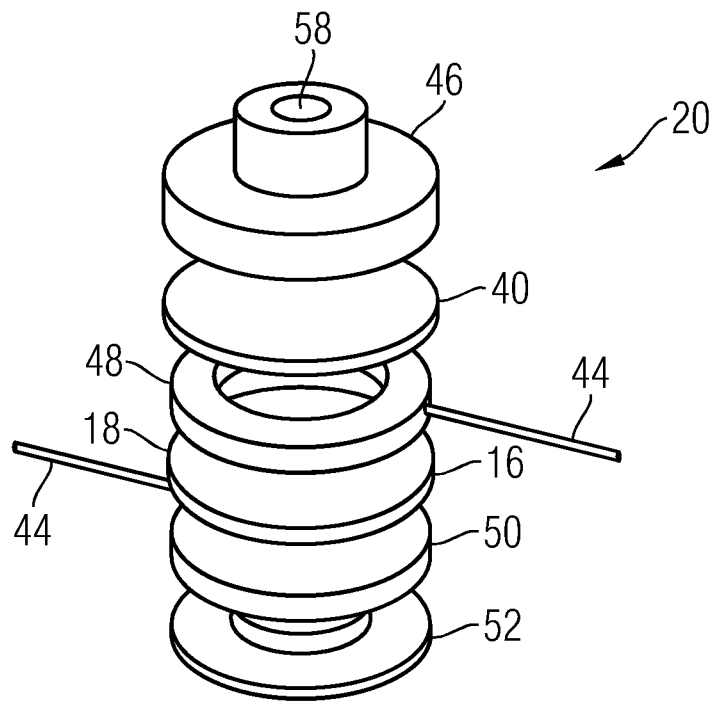
FIG. 6 schematically illustrate an apparatus for concentrating microobjects and for transferring them to another device.
Figure 6B:
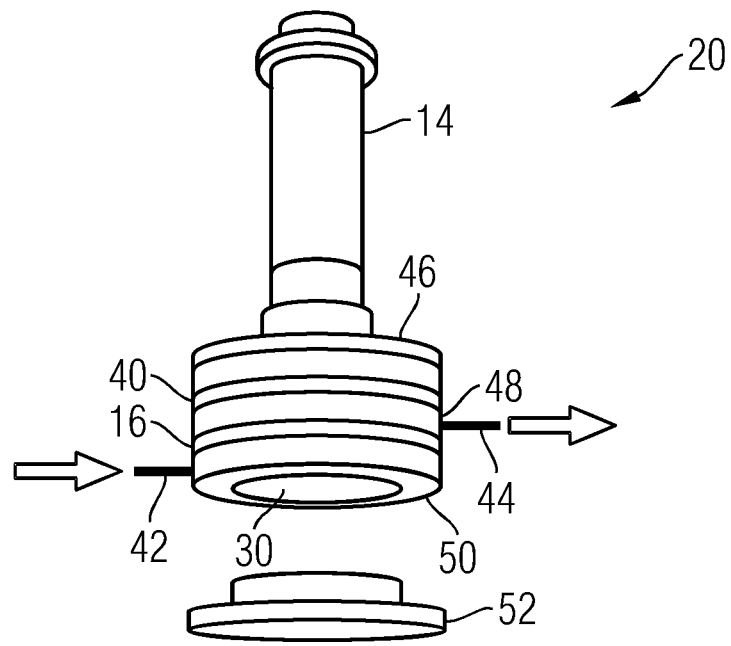

Referring now to FIG. 6, there is shown a macro-to-microfluidic filter device 20 for reducing the volume of a sample fluid containing organic microobjects, by removing the largest part of the fluid from the microobjects. The device 20 comprises a syringe lock or cover plate 46, a syringe piston 14, an inlet 58, a prefilter 40 (upper filter), a first ring 48, a first filter 16 (lower filter), a second ring 50, an outlet 30, a bottom plate or plug 52, a microfluidic inlet 42 and a micro fluidic outlet 44. The microfluidic outlet 44 connects to a space downstream of the prefilter 40 and upstream of the lower filter 16. The microfluidic inlet 42 connects to a space downstream of the lower filter 16. The device 20 is operated as follows. A sample fluid having a volume of the order of 0.1 ml to 10 ml is introduced via the inlet 58 into a space upstream of the prefilter 40. The piston 14 is then pushed downward, forcing the sample fluid to flow through the prefilter 40 and then through the lower filter 16. The prefilter 40 separates out e.g. large mammalian cells. The lower filter 16 captures e.g. bacteria. The lower filter 16 has pores extending all the way through it. Thus the e.g. bacteria do not become stuck as could be the case for example with a membrane matrix. The lower filter 16 may, for example, be a polycarbonate ("Nucleopore") filter or a silicon membrane filter, e.g. as manufactured by fluXXion. In a subsequent second step, the plug 52 is inserted into the second ring 50 to close the macrofluidic outlet 30. At the same time a microfluidic channel, through the microfluidic inlet 42, along the lower filter 16, and through the microfluidic outlet 44, is opened. The bacteria on the lower filter 16 are then eluted in a microfluidic volume (e.g. 100 μl) of a transfer liquid that is forced through the microfluidic channel, e.g. by a piston (not shown). The entire bacteria can be eluted for further treatment, or only the DNA can be transferred with the transfer liquid. In the latter case, the transfer liquid (elution buffer) can also be a lysis buffer or lysis can take place by some other mechanism, such as on a Whatman ELUTE lysis paper, using heat or ultrasound. The micro- and macrofluidic channels can be opened and closed via e.g. valves (mechanically, thermally or otherwise activated) or, as illustrated in the Figure, by removing or inserting the plug 52.

Figure 7A:
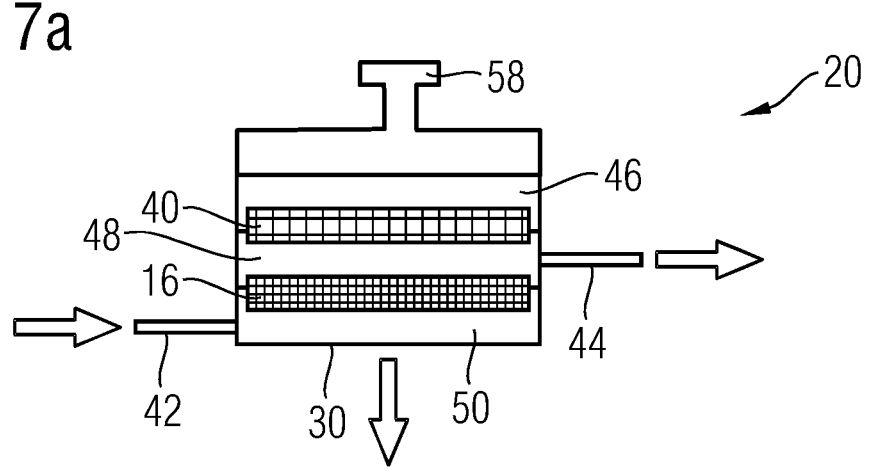
FIG. 7 schematically illustrate another apparatus for concentrating microobjects and for transferring them to another device.
Figure 7B:
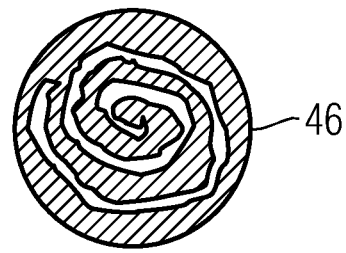
Figure 7C:
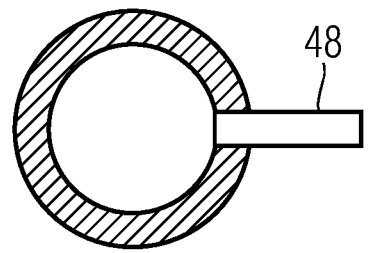
Figure 7D:
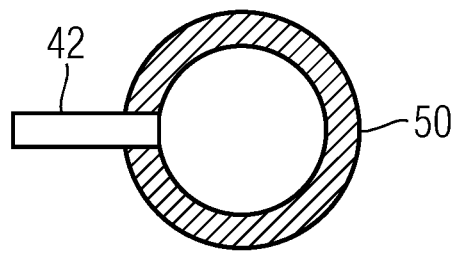

FIG. 7a is a schematic representation of a device 20 similar to the one described above with reference to FIG. 6. A liquid sample 10 having volume of around 1 to 5 ml is pushed through the device 20 by means of a syringe (not shown) and flows through the macroscopic passage 58, 40, 16, 30 including the prefilter 40 (upper filter) and the first filter 16 (lower filter). After closing the macroscopic passage, a pathogen stuck on the lower filter 16 is immersed in a transfer liquid (elution buffer) flowing into the device 20 via the microfluidic inlet 42, along the lower filter 16, and out of the device 20 via the microfluidic outlet 44. In the example shown, the cover plate 46 (shown distinctively in FIG. 7*b*), the upper ring 48 (shown distinctively in FIG. 7*c*) and the lower ring 50 (shown distinctively in FIG. 7*d*) are realized by means of double-sided adhesive tapes. In this case, the end of the macrofluidic passage can be closed by adhering tape to a solid substrate after the macrofluidic liquid (i.e. the fluid sample) has been pumped through. Also more than one fluidic connection can be integrated per tape. Alternatively, the parts of the device 20 which contain the prefilter 40 and the first filter 16, and which provide a housing, can be made of, for example, plastic.

Figure 8A:
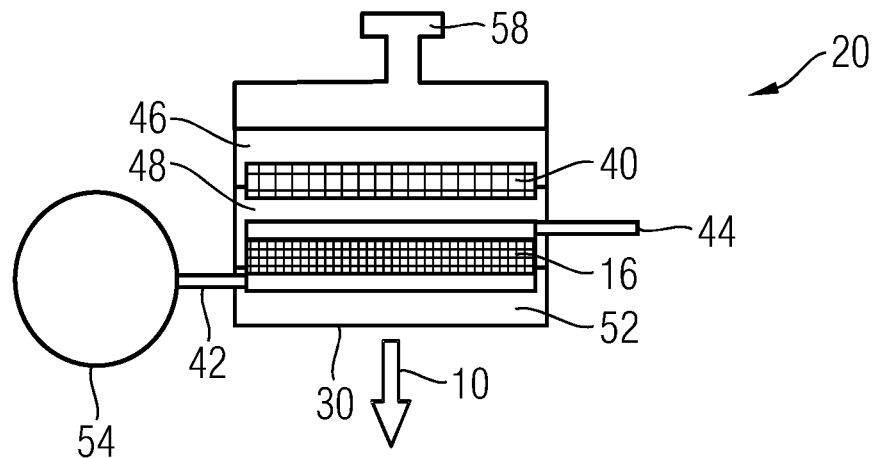
FIG. 8 schematically illustrate another apparatus for concentrating microobjects and for transferring them to another device.
Figure 8B:
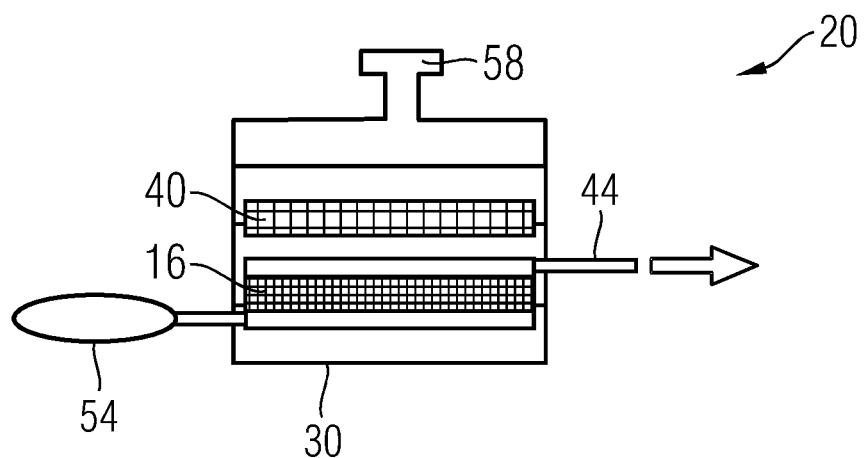

According to another embodiment, represented in FIG. 8, the transfer fluid is provided by a portion of the sample liquid 10 that has passed through the first filter 16. After accumulating the microobjects on the first filter 16, said portion of the sample liquid 10, i.e. the transfer fluid, is forced to flow back through the first filter 16 (in the upward direction in the Figure). This is achieved by compressing a chamber 54 containing e.g. water, air or oil (see FIG. 8*b*). The microobjects previously accumulated on the first filter 16 are thus immersed in the transfer fluid. The volume of the transfer fluid is by about an order of magnitude smaller than the volume of the sample liquid 10 that was initially introduced into the device 20. Thus the transfer fluid leaving the device 20 via the micro fluidic outlet 44 has a higher concentration of the microobjects. The transfer fluid can be processed further downstream, e.g. in a microfluidic chip connected to the microfluidic outlet 44. A valve (not shown in the Figure) may be arranged between the compressible chamber 54 and the space on the first filter 16 where the microobjects are accumulated. Both the valve and the compressible chamber can be controlled with e.g. temperature.

Figure 9:
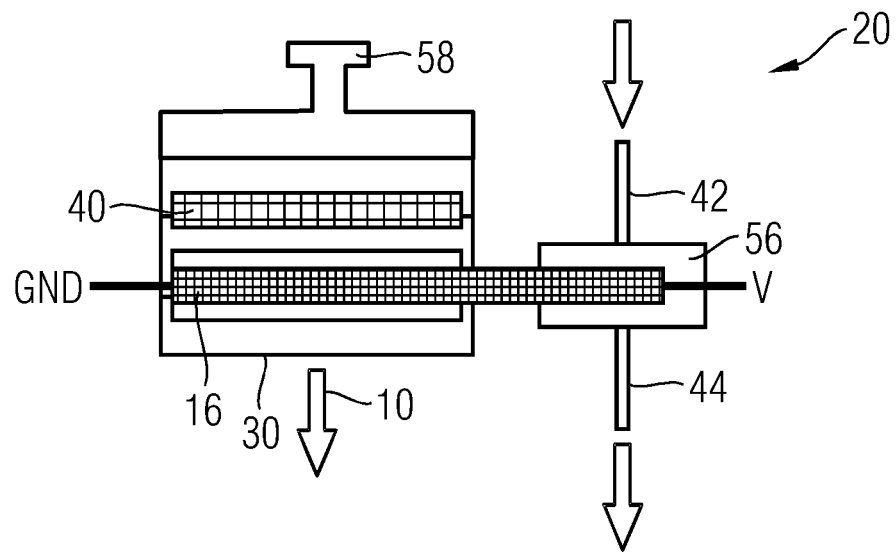
FIG. 9 schematically illustrates another apparatus for concentrating microobjects and for transferring them to another device.

In a different version of this scheme, illustrated in a simplified manner in FIG. 9, electrically charged or dipolar microobjects, such as bacteria or DNA, that have been trapped on or in the first filter 16, are transferred from the first filter 16 to a small chamber 56 via a DC or AC (dielectrophoresis) electric field. It is noted that bacteria generally carry a negative electric charge. The electric field can be generated by applying a voltage between the first filter 16 and the chamber 56. In the example shown, the first filter 16 is set to zero potential (GND) while the chamber is set to a positive potential (V). The chamber 56 can be connected to a microfluidic chip. The first filter 16 may comprise a gel material, e.g. a porous gel. Movement of the microobjects, e.g. bacteria or DNA, in a transverse (horizontal in the Figure) direction along or through the first filter 16 may thus be facilitated.

Figure 10:
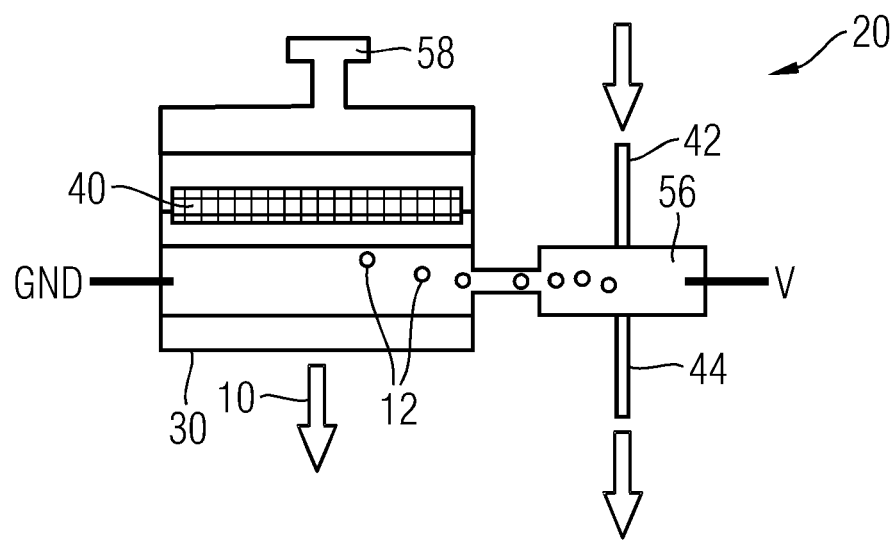
FIG. 10 schematically illustrates another apparatus for concentrating microobjects and for transferring them to another device.

Schematically represented in FIG. 10 is a device 20 according to another embodiment. The operating principle of the device 20 is similar to the one described above with reference to FIG. 9 in that the microobjects 12, after passing through the prefilter 40 (upper filter), are transferred to a small chamber 56. However, according to the present embodiment, the first filter 16 is absent. The electrical field separates the microobjects (e.g. bacteria) from the main flow (in the downward direction in the Figure) of the sample fluid 10 and transfers them into the chamber 56. A small gel plug may be provided to prevent the macroscopic flow (i.e. the flow of the sample fluid 10) from spreading into the chamber 56.

Figure 11A:
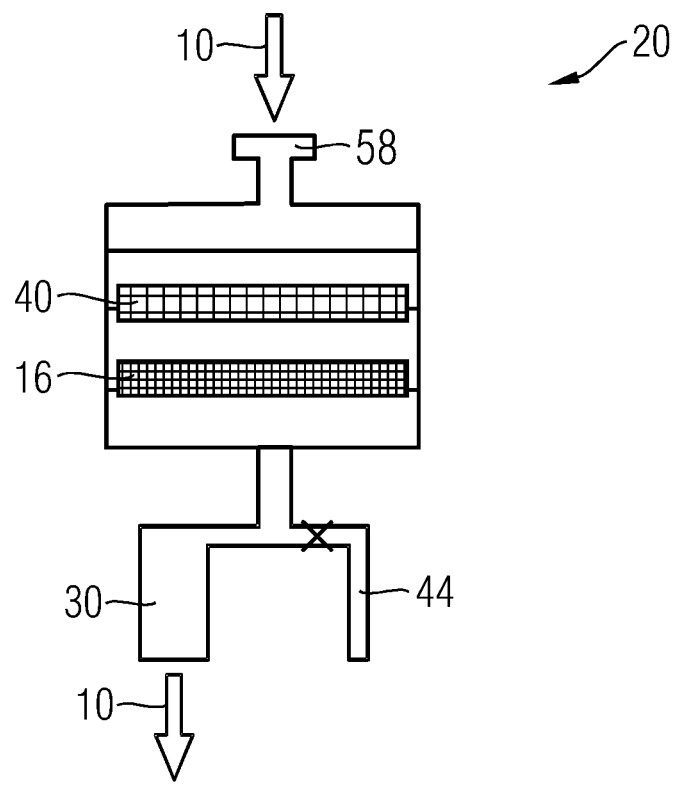
FIG. 11 schematically illustrate another apparatus for concentrating microobjects and for transferring them to another device.
Figure 11B:
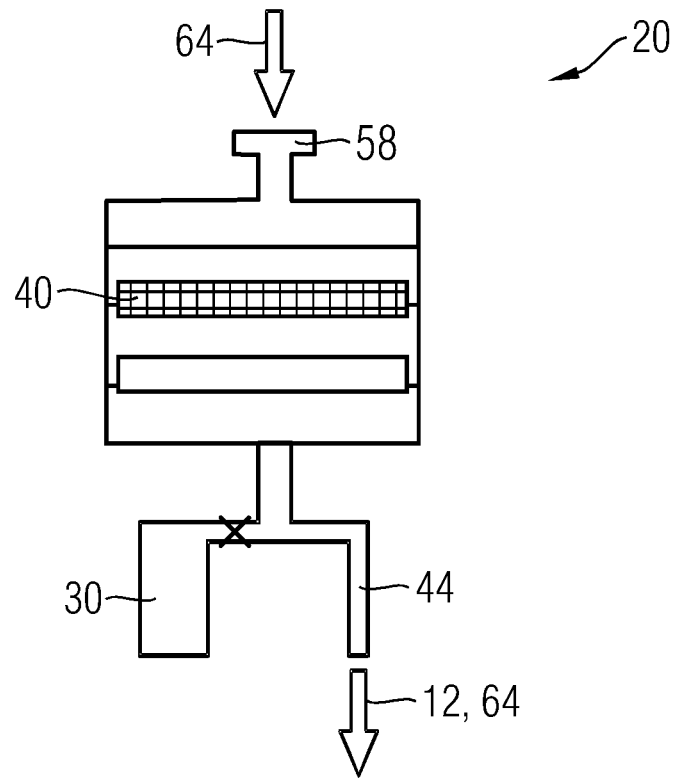

FIG. 11 illustrates yet another embodiment. The first filter 16, e.g. a membrane, is made of a filter material or gel that disintegrates in an acidic (high pH) or hot (high temperature) environment value. Examples of gels that dissolve at high pH are polyanions, such as (poly)acrylic acid and (poly)methacrylic acid (Y. Qiu and K. Park, Environment-sensitive hydrogels for drug delivery, Advanced Drug Delivery Reviews, vol. 53, pp.321-339, 2001). Temperature sensitive gels include co-polymers of (poly)ethylene oxide and (poly)propylene oxide (see the cited article by Qiu and Park). In a first step, illustrated in FIG. 11*a*, the sample fluid 10, of macroscopic volume, is pushed or sucked through the device 20 along a macroscopic channel 58, 40, 16, 30 comprising the inlet 58, the prefilter 40, the first filter 16, and a macrofluidic outlet 30. At the same time, a microfluidic outlet 44 remains closed, e.g. by means of a valve (not shown). In a second step, a small volume of NaOH is introduced into the device via the inlet 58. NaOH on its own or in combination with heat increases the pH and thereby breaks down the first filter 16. In addition, the NaOH may lyse the microobjects, e.g. bacteria, that were accumulated on the first filter 16, for example, to release DNA. In a third step, shown in FIG. 11*b*, the microfluidic outlet 44 is opened by means of the mentioned valve or by means of another valve (not shown). By blocking both the macrofluidic outlet 30 and the microfluidic outlet 44 for a while, a certain incubation time may be provided.

Experiments in which a microfluidic sample was prepared from a macrofluidic sample are described in the following.

Separation of human cells and bacteria using a prefilter and a first filter: *Escherichia coli* (*E coli*) were cultured over night in brain heart infusion and stained with the BacLight LIVE/DEAD stain. THP-1 cells were stained with a fluorescent marker. In this case the cell growth medium was exchanged for PBS in a centrifugation step. 500 µl of the bacterial suspension was mixed with 500 µl of human THP-1 cells in PBS. The 1 ml of cell+bacteria liquid was first filtered through a Whatman 5 µm pore size polycarbonate filter. 2 ml of air was used to remove the liquid from the filter. The filtrated suspension and the filter were analyzed using a fluorescence microscope. The 500 µl of the filtrate suspension was then filtrated a second time through a 0.22 millipore filter. With a 5× objective, only monocytes were detected, whereas the *E coli* were clearly seen with the 20×. As expected, the concentration of bacteria is much higher than the concentration of THP-1 cells in these samples (approx 109 vs. 106 cells/ml). The *E coli* were too many to count but the monocytes were at 5× magnification on average 26±4 cells/frame (3 frames). Frames from the 5× objective and the 20× objective showed the suspension after filtration through the 5 µm polycarbonate filter (prefilter). The prefilter removed most or all of the monocytes and allowed the bacteria to pass. However, a dead volume in the Whatman filter holder is rather large and about half of the sample was therefore lost there. With the 5× objective, the number of monocytes was 0 in all frames (4 frames). From plating experiments, it was seen that when filtering low concentrations of bacteria (<500 CFU/ml) through the 5 µm filters, roughly 100% of the bacteria pass, which shows that few if any bacteria stick to the polycarbonate filters. After the final filtration through the 0.22 µm filters, no more cells were found in the sample liquid.

Figure 12A:
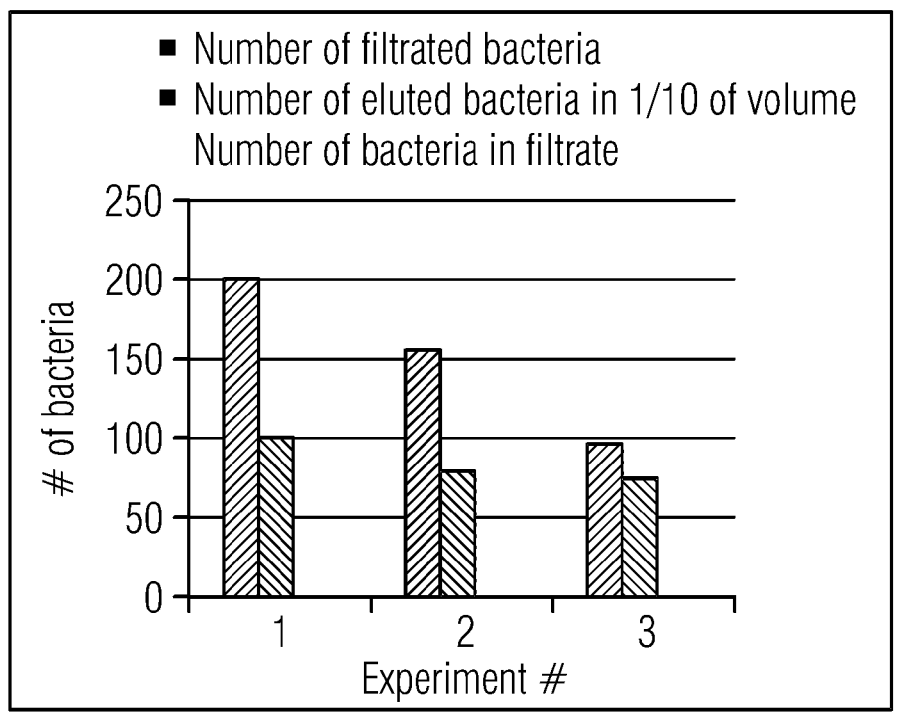
FIG. 12 show experimentally determined numbers and concentrations of bacteria.
Figure 12B:
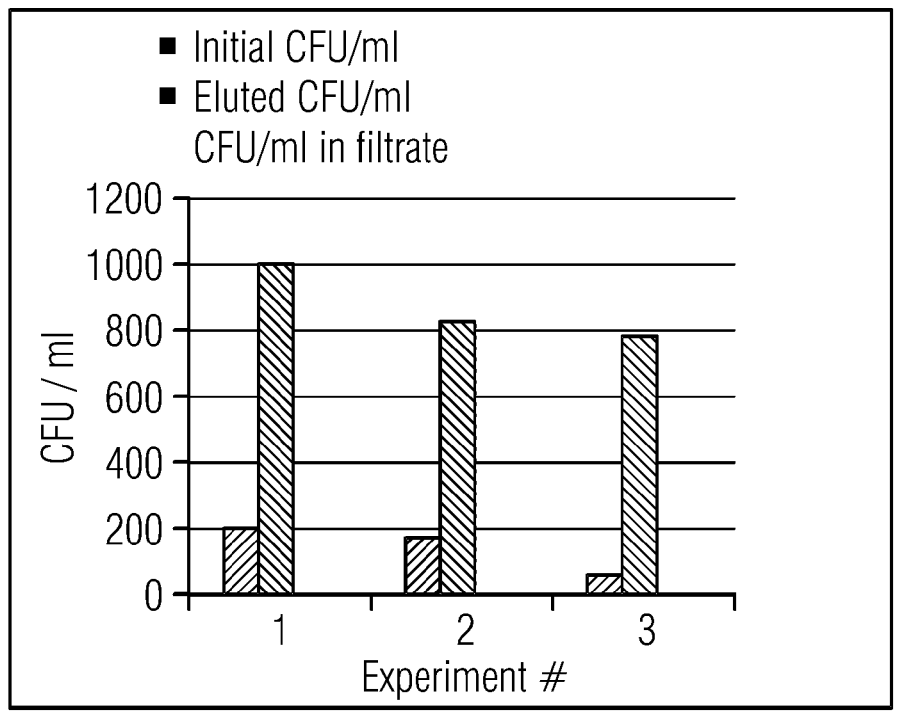

Up-concentration of bacteria by eluting 0.22 µm filter on bench: In a next step, we have also made experiments where the bacteria that have been captured on a 0.22 µm filter are subsequently eluted in a smaller volume to increase the concentration. Three such experiments have been conducted, with very similar results. With *E coli*, 500 µl of bacterial suspension was filtered through a 0.22 µm filter. The filter was then placed in 50 µl PBS buffer and vortexed. After 5 min, the filter was removed and the suspension cultured. The starting suspension contained ~200 CFU/ml (100 CFU in 500 µl) and the elution from the filter ~1000 CFU/ml (50 CFU in 50 µl), meaning a 5× up-concentration. Also *Staphylococcus aureus* (*S aureus*) have been filtered and eluted in the same way (vortex in smaller volume+wait 5 min). In these experiments, 1 ml of suspensions with 160 and 98 CFU/ml, respectively, were filtered through 0.22 µm filters. The bacteria where then eluted in 100 µl of TBS growth medium and cultured. The number of *S aureus* in the 100 µl medium was in this case 84 ('840 CFU/ml') and 78 ('780 CFU/ml'), respectively. Thus, the final concentration after these experiments was 525% and 795% of the starting concentration. The filtrate (solution that passes filter) was also cultured as a control and resulted in 0 colonies in all the above experiments. The results are summarized in FIGS. 12.

Figure 13:
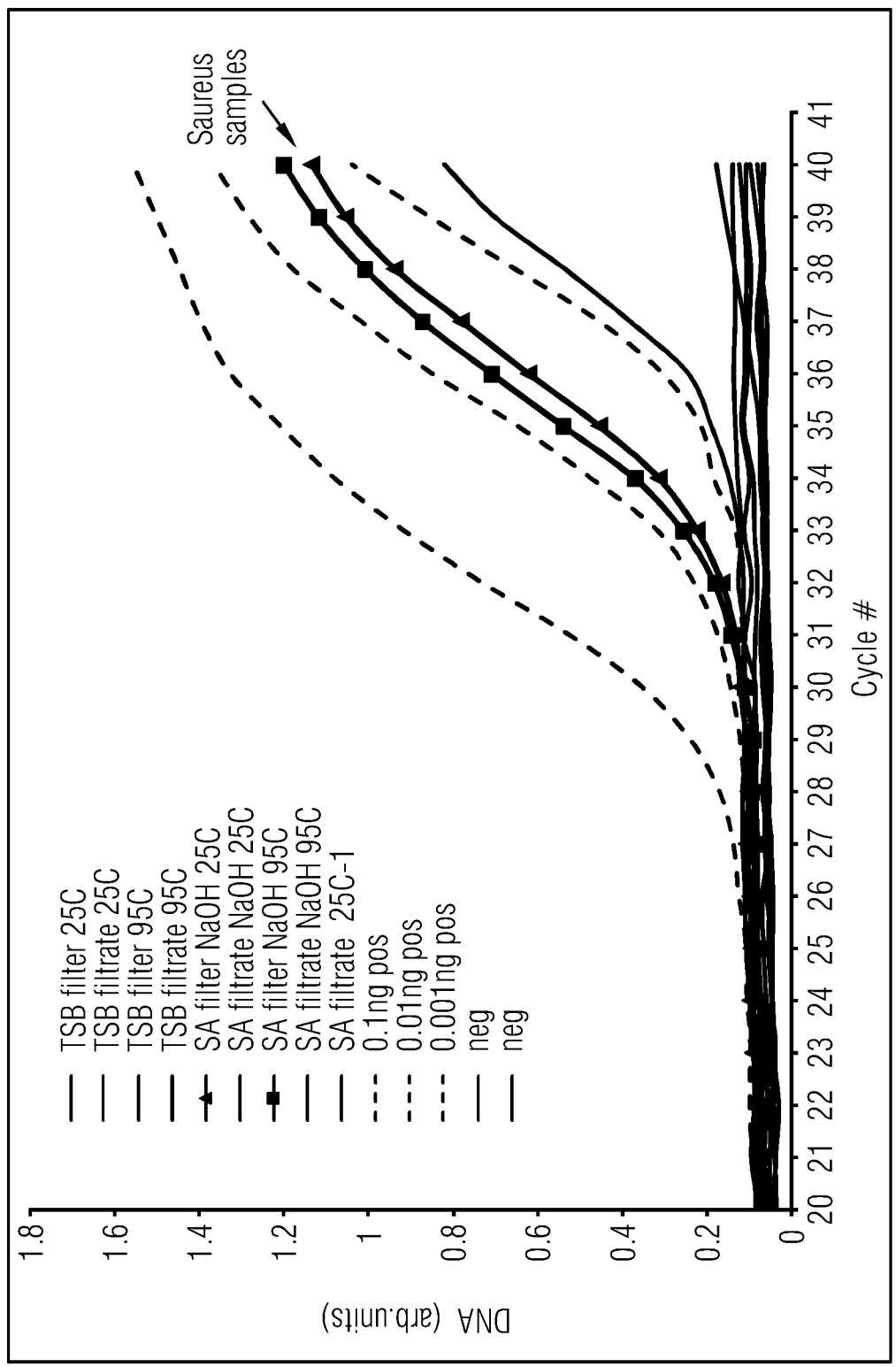
FIG. 13 shows amounts of DNA collected with different filters.

NaOH lysis and elution on bench: In similar experiments as described above, the filters with captured *S aureus* from 1 ml of the bacterial suspension, containing 98 CFU/ml, have been placed in 100 µl NaOH, vortexed and incubated for 5 min. Thereafter, the filters were removed and the DNA in the NaOH was extracted with ethanol precipitation. FIG. 13 summarizes the corresponding qPCR results. Bacteria caught on 0.22 µm filters were simultaneously lysed and eluted with NaOH. As seen from the SA filter-samples, a significant amount of *S aureus* DNA is eluted. A significant amount (close to the 0.01 ng reference) of *S aureus* DNA were recovered from both filters that should capture bacteria ('SA filter NaOH 25C' and 'SA filter NaOH 95C'), when starting with only 98 bacteria per ml. Apart from one filter that was used with only TSB medium (TSB filter 25C'), all negative controls and filtrates showed little or no DNA content.

Figure 14:
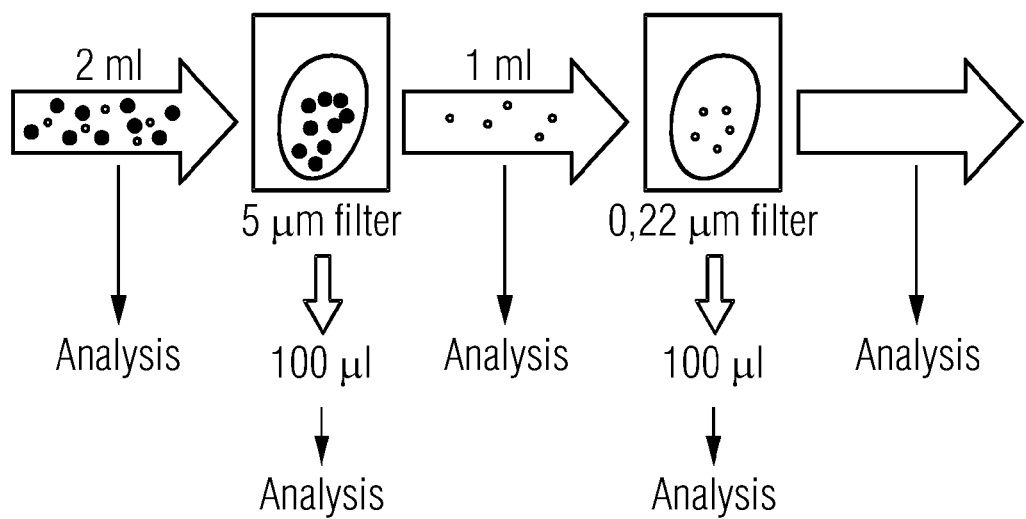
FIG. 14 schematically illustrates a method for separating bacteria and human cells.
Figure 15:
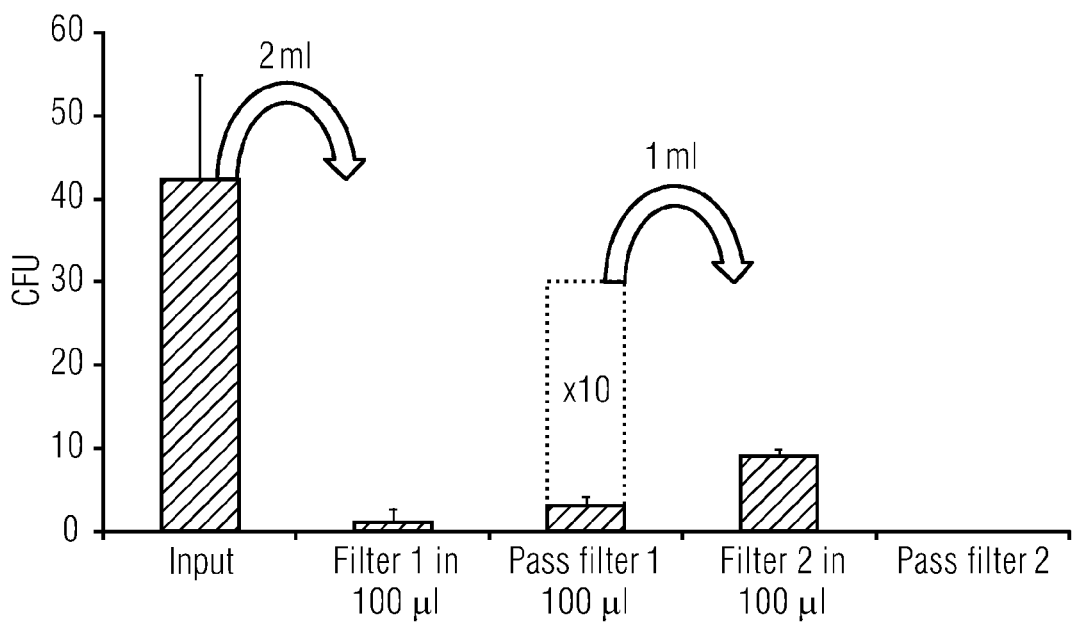
FIG. 15 shows the number of colony forming units (CFU) of S aureus bacteria at different stages during a filtering process.
Figure 16:
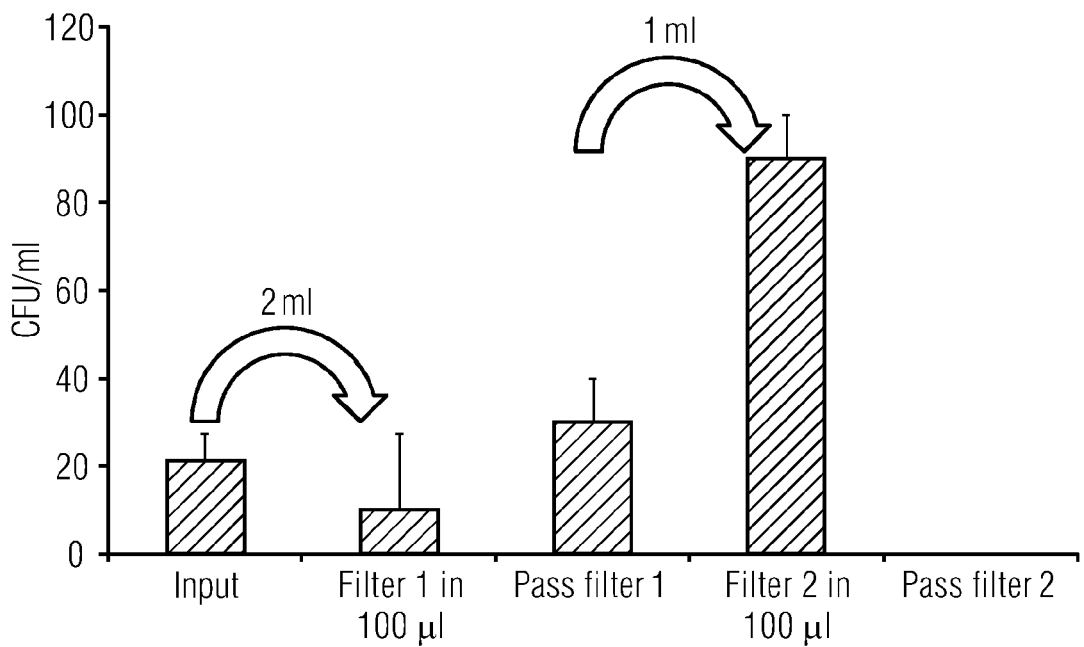
FIG. 16 shows the number of colony forming units (CFU) of S aureus bacteria at different stages during a filtering process.

Up-concentration of bacteria and separation from human cells: FIG. 14 illustrates an experimental scheme for separating bacteria and human cells, followed by enrichment on the second filter. In a corresponding filtering experiment with two filters (5 µm and 0.22 µm), the input liquid was a mixed solution of 10000 U937 human cells/ml and 22 *S aureus* / ml. 2 ml of the mixed sample solution was filtered through a 5 µm filter. 1 ml of this filtrate was subsequently filtered through a 0.22 µm filter. Bacteria were eluted from both filters in 100 l medium for 5 minutes. Samples from all stages of the filtering sequence were analyzed through culturing. The results of the experiment are shown in FIGS. 15 and 16. Due to the "dead volume" of the filter holders that were used, not all liquid that passed the first filter could go through the second filter. However, almost no bacteria were lost on the first filter and the elution from the second filter had a significantly higher concentration of *S aureus* compared to the input sample. Taken together, the above experiments prove that the combination of filters can be used to separate bacteria from human cells and increase the concentration of bacteria by reducing the sample volume.

FIG. 15 shows the absolute numbers of *S aureus* at each stage of the filtering process. Note that only half of the filtrate from filter 1 is used as input liquid to filter 2. 100 pl of this filtrate was cultured for analysis but 1 ml was filtered through filter 2. No bacteria could be detected in the filtrate of filter 2.

FIG. 16 shows the concentration of *S aureus* at each stage of the filtering process. The concentration in 'Pass filter 1' should be equal to or less than the input concentration. The slightly over-estimated value is due to that the concentration is calculated from analysis of only 100 µl (containing on average 3 bacteria in this case). No bacteria could be detected in the filtrate of filter 2.

To summarize, particular techniques are proposed for reducing an initial sample volume from ml to µl, without losing significant numbers of bacteria for further analysis. The ml volume thus obtained can be further analyzed using a microfluidic lab-on-a-chip systems, or be imaging in a single capture by an optical microscope, especially when a low concentration of bacteria makes it necessary to start with a "large" volume of sample liquid.

The invention may find application in rapid microbiological analysis for industrial applications (food processing, pharmaceutical, personal care products, beverage, environmental, and industrial process sectors) as well as for clinical applications. The proposed method may be particularly well suited for detecting and enumerating microorganisms. Furthermore, the use of specific stains (e.g. immunolabeling) may offer a route to selective detection and identification. A particular application of the invention may be on-chip detection of bacteria causing infectious diseases and screening for antibiotic susceptibility. Other applications are e.g. food and water quality testing as well as detection of viruses in mammalian cells.

The invention is proposed within the framework of the research projects "Xyall: Digital cell imaging for life sciences and pathology" and is related to the Rapid MicroBiology venture in the Healthcare Incubator.

While the invention has been illustrated and described in detail in the drawings and in the foregoing description, the drawings and the description are to be considered exemplary and not restrictive. The invention is not limited to the disclosed embodiments. Equivalents, combinations, and modifications not described above may also be realized without departing from the scope of the invention.

The verb "to comprise" and its derivatives do not exclude the presence of other steps or elements in the matter the "comprise" refers to. The indefinite article "a" or "an" does not exclude a plurality of the subjects the article refers to. In particular, the term "microobjects" does not exclude the presence of other microobjects. For example, the sample fluid 10 may, in addition to the microobjects referred to in claim 1, comprise microobjects which are not transferred to the second filter 32 or which are lost during the process.

It is also noted that a single unit may provide the functions of several means mentioned in the claims. The mere fact that certain features are recited in mutually different dependent claims does not indicate that a combination of these features cannot be used to advantage. Any reference signs in the claims should not be construed as limiting the scope.

The invention claimed is:

1. A method of analyzing a sample fluid containing organic microobjects, the method comprising the steps of:
   up-concentrating the microobjects by removing, in a total time $T_1$, a volume $V_1$ of the sample fluid from the microobjects;
   immersing the microobjects in a transfer fluid; or leaving the microobjects in a remaining portion of the sample fluid, the remaining portion of the sample fluid then providing the transfer fluid;
   filtering, in a total time $T_3$, a volume $V_3$ of the transfer fluid by a filter, thereby accumulating the microobjects on the filter; and
   generating a microscopic image of the microobjects accumulated on the filter;
   wherein the throughput $V_1/T_1$ of the step of up-concentrating is greater than the throughput $V_3/T_3$ of the filtering step.

2. A method according to claim 1, wherein the up-concentrating step is performed using a first filter and the filtering step is performed using a second filter, the first filter having a larger area than the second filter.

3. The method as set forth in claim 1, wherein the time spent on the steps of up-concentrating, immersing, filtering, and generating the image is shorter than the time spent on filtering the entire sample fluid by the filter and imaging the microobjects on that filter.

4. The method as set forth in claim 1, wherein $V_3$ is less than $0.2 * V_1$.

5. The method as set forth in claim 1, comprising a step of
prefiltering the sample fluid by a prefilter, the prefilter retaining at most an insignificant fraction of the microobjects;
the step of prefiltering being performed prior to the step of filtering.

6. The method as set forth in claim 1, wherein the filter is a second filter and the step of up-concentrating involves:
filtering the sample fluid by a first filter, thereby accumulating the microobjects on the first filter;
dissolving the first filter.

7. The method as set forth in claim 6, wherein the step of immersing involves:
the transfer fluid flowing along the first filter; or
a portion of the sample fluid flowing back through the first filter.

8. The method as set forth in claim 1, wherein the step of up-concentrating involves:
evaporating the volume $V_1$ of the sample fluid; and/or
attracting the microobjects to a collection zone; and/or
centrifugalizing the sample fluid.

9. The method as set forth in claim 1, wherein generating the image involves:
generating an optical image of the microobjects; or
scanning the microobjects.

10. The method as set forth in claim 1, comprising
releasing a dye into the sample fluid or into the transfer fluid.

11. The method of claim 1 wherein the filter is sized so that the entire filter fits into a field of view of a microscope objective.

12. The method of claim 1 wherein the microobjects are left in a remaining portion of the sample fluid and the remaining portion of the sample fluid provides the transfer fluid.

13. The method of claim 1 wherein the sample fluid is a liquid and the up-concentrating of the microobjects is performed by removing, in a total time T1, a volume V1 of the sample liquid from the microobjects.

* * * * *